(12) United States Patent
O'Lenick, Jr. et al.

(10) Patent No.: US 8,124,062 B2
(45) Date of Patent: Feb. 28, 2012

(54) DIMER ALKYL SILICONE POLYMERS IN PERSONAL CARE APPLICATIONS

(75) Inventors: Anthony J. O'Lenick, Jr., Dacula, GA (US); Kevin A. O'Lenick, Dacula, GA (US)

(73) Assignee: SILTECH Corporation, Toronto, Ontario (CA)

( * ) Notice: Subject to any disclaimer, the term of this patent is extended or adjusted under 35 U.S.C. 154(b) by 72 days.

(21) Appl. No.: 12/807,001

(22) Filed: Aug. 26, 2010

(65) Prior Publication Data

US 2011/0033408 A1     Feb. 10, 2011

Related U.S. Application Data

(63) Continuation-in-part of application No. 12/384,682, filed on Apr. 9, 2009, now Pat. No. 7,811,976.

(51) Int. Cl.
  *A61Q 5/12* (2006.01)
(52) U.S. Cl. ............ 424/70.12; 528/25; 528/31; 528/32
(58) Field of Classification Search .................. None
  See application file for complete search history.

(56) References Cited

U.S. PATENT DOCUMENTS

| 5,493,041 | A  | * | 2/1996  | Biggs et al. .................... 556/453 |
| 5,505,937 | A  | * | 4/1996  | Castrogiovanni et al. ...... 424/64 |
| 2001/0041771 | A1 | * | 11/2001 | Kondo et al. ................. 525/100 |
| 2006/0293431 | A1 | * | 12/2006 | Kani et al. .................... 524/492 |

FOREIGN PATENT DOCUMENTS

JP    2008-115358    *    5/2008

OTHER PUBLICATIONS

Abstract for JP 2008-115358 (May 2008).*
Machine generated translation of JP 2008-115358 into English (May 2008).*

* cited by examiner

*Primary Examiner* — Marc Zimmer

(57) ABSTRACT

This invention relates to a novel class of Dimer Alkyl Silicone Polymers (DASP) and their use to provide conditioning to skin and hair. By conditioning is meant a elegant smooth skin feel, eliminating dryness and raspiness. It is thought the mechanism of action is related to the fact that the DASP compounds reduce surface tension of personal care products, providing outstanding conditioning and skin feel. The improved conditioning composition based upon a very specific class of dimer alkyl silicone polymers (DASP) that despite their solubility in oil, lower surface tension and improve conditioning of personal care products.

6 Claims, No Drawings

DIMER ALKYL SILICONE POLYMERS IN PERSONAL CARE APPLICATIONS

RELATED APPLICATIONS

This application is a continuation in part of U.S. patent application Ser. No. 12/384,682, filed Apr. 9, 2009 now U.S. Pat. No. 7,811,976.

FIELD OF THE INVENTION

This invention relates to a novel class of Dimer Alkyl Silicone Polymers (DASP) and their use to provide conditioning to skin and hair. By conditioning is meant a elegant smooth skin feel, eliminating dryness and raspiness. It is thought the mechanism of action is related to the fact that the DASP compounds reduce surface tension of personal care products, providing outstanding conditioning and skin feel. The improved conditioning composition based upon a very specific class of dimer alkyl silicone polymers (DASP) that despite their solubility in oil lower surface tension and improve conditioning of personal care products.

This invention is a process for providing conditioning to hair and skin which comprises contacting the skin with an effective conditioning concentration of a very specific class of dimer alkyl silicone polymers (DASP).

This invention relates to cosmetic products containing the oil soluble, surface tension reducing dimer alkyl silicone polymers (DASP).

BACKGROUND OF THE INVENTION

The DASP of the present invention are useful in serums, creams and lotions, lipsticks and other personal care products, either oil based or emulsions.

The products lower the surface tension of the oil phases to which they are added and despite their oil solubility, rather than silicone solubility, offer silicone feel and aesthetics to personal care formulations. Key to this performance is the presence of the alkyl group that provides solubility in the oil phase (by oil phase is meant a material insoluble in both silicone fluid and water).

Silicone fluids offer exceptionally low surface tension, in the area of 20 dynes/cm, but are insoluble in oils (both hydrocarbon and ester). Oils have a surface tension of around 30 dynes/cm and have a greasy feel. The compounds of the present invention when added to cosmetic oils lower the surface tension and provide outstanding skin feel, transfer resistance to lipsticks and conditioning effects to the hair and skin.

Another application of the compounds of the present invention is to reduce or eliminate syneresis in stick products. Lipsticks contain many water insoluble materials, including esters, hydrocarbons and silicone. Since silicone is insoluble in these systems, they bleed to the surface and cause sweating or syneresis, which is highly undesirable to the consumer. Incorporation of between 0.1 and 10% of the compounds of the present invention eliminate this problem.

Additionally, when added to pigmented products, these materials have an ability to coat the pigment and minimize the deposit of the pigments on glass, making the highly desirable transfer resistant lipstick without the need for expensive resins.

Additionally, the ability to lower surface tension of the conditioner applied to the skin that has a surface tension below 30 dynes/cm has been elusive since organic materials from which they are based have this value as the lower limit of surface tension achievable. Lower surface tension makes for better lubrication, and slip, resulting in improved skin feel.

Lower surface tension can only be achieved by using dimethyl silicones (also known as silicone fluids), but these polymers are not soluble in oils and have not been used. The present invention relates to including two very key groups on the silicone polymer, the first an alkyl group, improving the solubility of the silicone in oil, and also a very limited crosslink density that despite clarity in the oil results in the lowest free energy of the oil to be when the silicone polymer is pushed to the oil skin interface, where it surprisingly lowers surface tension.

The use of the compounds of the present invention, which have been found to be patentable, have not been used as conditioners in personal care applications.

SUMMARY OF THE INVENTION

The present invention discloses a series of dimer alkyl silicone polymers (DASP) and a process for their use in personal care applications. Said process comprises contacting the hair or skin with an effective conditioning concentration of the DASP compounds.

DETAILED DESCRIPTION OF THE INVENTION

The present invention is a process for conditioning hair or skin, which comprises contacting the hair or skin with an effective conditioning concentration of a polymer conforming the following structure;

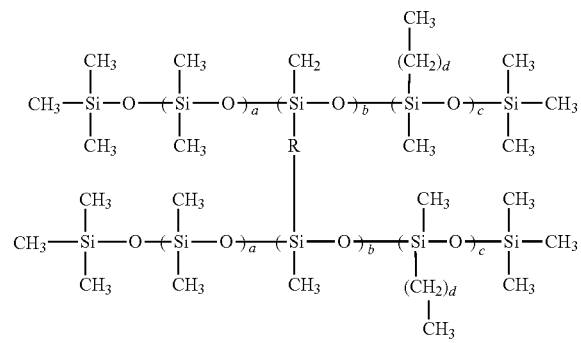

wherein:
a is an integer ranging from 1 to 200;
b is 1;
c is an integer ranging from 1 to 20;
d is an integer ranging from 11 to 15;
with the proviso that the ratio of a to c ranges from 1:1 to 10:1;
R is

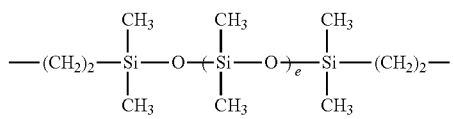

e is an integer ranging from 10 to 100.

The range of the a, b, c, d and e values are all critical to functionality. The value of "a" determines the amount of silicone nature in the molecule which critically effects surface tension. Too low the surface tension is not reduced, too high the material becomes insoluble in the oil.

The value of "b" critically effects the viscosity and solubility of the material in oils. As the value of "b" is increased to 2 or 3 a hard gel results. Not wanting to be held to any one theory we believe the formation of the prescribes dimer (that is di product) results in a molecule that is large enough to be driven to the metal oil surface and small enough to be soluble.

The value of "c" determines the solubility of the DASP in the oil.

The value of "e" determines the viscosity of the DASP. Below 11, there is minimal solubility, above 15 the molecules become solid and destroy the lubrication.

The ranges of the values for a relative to b relative to c relative to d, keep the molecule in balance, providing the balance between surface tension reduction and solubility.

PREFERRED EMBODIMENT

In a preferred embodiment d is 11.
In a preferred embodiment d is 15.
In a preferred embodiment the ratio of a to c ranges from 1:1 to 1:5.
In a preferred embodiment the ratio of a to c is 1:4.
In a preferred embodiment the ratio of a to c is 1:3.

EXAMPLES

Silanic Hydrogen Compounds

The silanic hydrogen compounds of the present invention conform to the following structure and are available from Siltech LLC sold under the Silmer® H trade name.

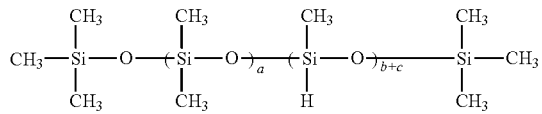

b+c is an integer ranging from 2 to 21;
a is an integer ranging from 1 to 20;
with the proviso that the ratio of a to c ranges from 1:1 to 10:1

| Example | b + c | a | Ratio a:c |
|---------|-------|-----|-----------|
| 1 | 2 | 1 | 1:1 |
| 2 | 9 | 32 | 1:4 |
| 3 | 11 | 50 | 1:5 |
| 4 | 16 | 150 | 1:10 |
| 5 | 21 | 160 | 1:8 |

Vinyl Crosslinkers

Vinyl crosslinkers are items of commerce available from Siltech LLC sold under the trade name Silmer® VIN. They conform to the following structure:

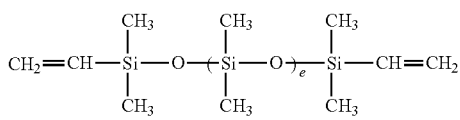

e is an integer ranging from 10 to 100.

| Example | e |
|---------|-----|
| 6 | 100 |
| 7 | 75 |
| 8 | 50 |
| 9 | 25 |
| 10 | 10 |

Alpha Olefin

Alpha olefins are items of commerce. They are available from a variety of sources including Chevron. They conform to the following structure:

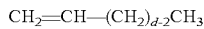

$CH_2\!=\!CH\!-\!(CH_2)_{d-2}CH_3$ d is an integer ranging from 11 to 15;

| Example | d |
|---------|-----|
| 11 | 11 |
| 12 | 13 |
| 13 | 15 |

Hydrosilylation

Hydrosilylation is a process that reacts terminal vinyl compounds with silanic hydrogen to obtain a Si—C bond. References to this reaction, incorporated herein by reference, include:

U.S. Pat. Nos. 3,715,334 and 3,775,452 to Karstedt, shows the use of Pt(O) complex with vinylsilicon siloxane ligands as an active hydrosilylation catalyst.

Additional platinum complexes, such as complexes with platinum halides are shown by, U.S. Pat. No. 3,159,601 Ashby and, U.S. Pat. No. 3,220,972, to Lamoreaux.

Another hydrosilylation catalyst is shown by Fish, U.S. Pat. No. 3,576,027. Fish prepares a platinum(IV) catalyst by reacting crystalline platinum(IV) chloroplatinic acid and organic silane or siloxane to form a stable reactive platinum hydrosilylation catalyst.

General Procedure

To the specified number of grams of the specified silanic hydrogen compound (Examples 1-5) is added the specified number of grams of the specified vinyl compound (Example 6-10). The mass is mixed well. To that mixture is added 0.1% Karstedt catalyst, which is commercially available from Geleste. The agitation is stopped and the reaction begins. The reaction is held at 80° C. for one hour. To that mixture is added the specified number of grams of the specified alpha olefin (Example 11-13). The reaction is held at 80° C. for 4 hours. The product is used without purification.

Examples 14-23

| Example | Silanic Hydrogen | | Vinyl Compound | | Alpha Olefin | |
|---------|---------|--------|---------|--------|---------|--------|
| | Example | Grams | Example | Grams | Example | Grams |
| 14 | 1 | 358 | 6 | 3794 | 11 | 168 |
| 15 | 2 | 307 | 7 | 267 | 12 | 627 |
| 16 | 3 | 452 | 8 | 194 | 13 | 1120 |
| 17 | 4 | 122 | 9 | 111 | 11 | 2520 |
| 18 | 5 | 1272 | 10 | 47 | 12 | 3136 |
| 19 | 1 | 354 | 10 | 464 | 13 | 224 |
| 20 | 2 | 307 | 9 | 111 | 13 | 707 |

-continued

| Exam- | Silanic Hydrogen | | Vinyl Compound | | Alpha Olefin | |
|---|---|---|---|---|---|---|
| ple | Example | Grams | Example | Grams | Example | Grams |
| 21 | 3 | 452 | 8 | 194 | 12 | 980 |
| 22 | 4 | 127 | 7 | 287 | 11 | 2820 |
| 23 | 5 | 1272 | 6 | 379 | 13 | 258 |

The compounds so prepared are clear liquids and are added to a variety of oils to lower surface tension.

| Transfer Resistant Lipstick ANH8-10-1 | |
|---|---|
| Ingredient | % |
| Triisostearyl Citrate | 5.00 |
| Polyglyceryl-3 Diisostearate | 0.50 |
| Carnauba Wax | 6.50 |
| Ozokerite | 16.00 |
| Microcrystalline Wax | 6.00 |
| Polyethylene | 1.00 |
| Isododecane | 35.00 |
| Example 21 | 10.00 |
| Bismuth Oxychloride | 6.00 |
| Mica, Methicone | 9.00 |
| Color Grind | |
| Red 6 Lake | 0.40 |
| Red 7 Lake | 0.20 |
| Titanium Dioxide | 0.33 |
| Iron Oxides (yellow) | 0.10 |
| Iron Oxides (red) | 0.17 |
| Tri octyldodecyl citrate | 3.80 |
| | 100.00 |

| Transfer Resistant Lipstick ANH8-10-2 | |
|---|---|
| Ingredient | % |
| Triisostearyl Citrate | 15.00 |
| Polyglyceryl-3 Diisostearate | 0.50 |
| Carnauba Wax | 6.50 |
| Ozokerite | 16.00 |
| Microcrystalline Wax | 6.00 |
| Polyethylene | 1.00 |
| Isododecane | 35.00 |
| Bismuth Oxychloride | 6.00 |
| Mica, Methicone | 9.00 |
| Color Grind | |
| Red 6 Lake | 0.40 |
| Red 7 Lake | 0.20 |
| Titanium Dioxide | 0.33 |
| Iron Oxides (yellow) | 0.10 |
| Iron Oxides (red) | 0.17 |
| Tri octyldodecyl citrate | 3.80 |
| | 100.00 |

Manufacturing Procedure:

Prepare color grind in advance, by combining the oil and pigment with stirring. Mill over a three roll mill until the agglomerates are reduced to under 10 μm.

Combine the waxes and oils in a closed kettle equipped with a high speed agitator and a side sweep mixer. Heat to 95-100° C. with stirring until clear. Add the Biron LF-2000 and the D;9051/I. Mill at high speed until dispersed. Add the color grind. Mill at high speed for one minute. Stir batch, allowing it to cool to 70° C. Drop the batch or proceed directly to fill into suitable hermetically sealed cases.

ANH8-10-2 was found to provide non-transfer resistant properties, whilst ANH8-10-1 transferred pigment under the same test conditions to a coffee cup when the lips to which the formulation was applied were pressed to it. Most importantly, example AHH8-10-2 provided conditioning to the skin (lips) (i.e. it had a elegant softening effect).

| Lip Balm with SPF & Vitamins Formulation A | |
|---|---|
| Component | wt % |
| Petrolatum | 63.65 |
| Sorbeth 2 oleate | 10.00 |
| Ascorbic Acid Vitamin C | 0.10 |
| Octyl Methoxycinnamate | 7.50 |
| Octocrylene | 7.00 |
| Oxybenzone | 6.00 |
| Octyl Salicylate | 5.00 |
| Tocopherol Vitamin E | 0.25 |
| Grapefruit Fragrance | 0.50 |

| Lip Balm with SPF & Vitamins Formulation B | |
|---|---|
| Component | wt % |
| Petrolatum | 53.65 |
| Example 20 | 10.00 |
| Sorbeth 2 oleate | 10.00 |
| Ascorbic Acid Vitamin C | 0.10 |
| Octyl Methoxycinnamate | 7.50 |
| Octocrylene | 7.00 |
| Oxybenzone | 6.00 |
| Octyl Salicylate | 5.00 |
| Tocopherol Vitamin E | 0.25 |
| Grapefruit Fragrance | 0.50 |

Procedure:
1. Disperse the Vitamin C in the sorbeth 2 oleate
2. Melt Petrolatum and add sunscreens and mixture (1).
3. When product is clear add Vitamin E and Fragrance.
4. Cool and Fill.

Formulation B was found to be more silicone like elegant and Formulation A. Formulation B had a surface tension of 26 dynes/cm, whilst Formulation A had a surface tension of 32 dynes/cm. Most importantly, example B provided conditioning to the skin (i.e. it had a elegant softening effect).

| Sunscreen Lotion Example A | |
|---|---|
| Component | wt % |
| Water | 49.5 |
| Polysurf 67 CF | 0.5 |
| Propylene Glycol | 2.0 |
| Tetrasodium EDTA Versene 100 | 0.4 |
| Octocrylene | 7.5 |
| Oxybenzone | 3.0 |
| Avobenzone | 2.0 |
| Lauryl PEG 8 dimethicone | 4.0 |
| Example 18 | 5.0 |
| Hexamethyl Disiloxane | 25.0 |
| Propylparaben | 0.2 |
| Methylparaben | 0.4 |
| Fragrance | 0.5 |

| Sunscreen Lotion Example B | |
|---|---|
| Component | wt % |
| Water | 49.5 |
| Polysurf 67 CF | 0.5 |
| Propylene Glycol | 2.0 |
| Tetrasodium EDTA | 0.4 |
| Octocrylene | 7.5 |
| Oxybenzone | 3.0 |
| Avobenzone | 2.0 |
| Lauryl PEG 8 dimethicone | 4.0 |
| Cetyl dimethicone | 5.0 |
| Hexamethyl Disiloxane | 25.0 |
| Propylparaben | 0.2 |
| Methylparaben | 0.4 |
| Fragrance | 0.5 |

Procedure:

1. Heat water to 75-80° C. and dissolve the Polysurf (polyacrylate). Mix until completely dissolved.
2. Cool to 50° C.
3. Add Propylene Glycol and EDTA to water.
4. Mix Sunscreens, lauryl PEG 8 dimethicone, cetyl dimethicone or Example 18 and Parabens and heat to 55 C until all solids are completely dissolved.
5. Add hexamethyl disiloxane and maintain temperature at 50° C.
6. Add Sunscreen mixture to water phase with high speed mixer. Mix until uniform.
7. Cool to 35° C., add Fragrance.
8. Fill.

The formulation made using Example 18 (A) has a silicone like feel and conditions the skin, whilst the one with cetyl dimethicone does not.

| Shampoo Formulation 2 in 1 Shampoo (Coacervate) FH183A | |
|---|---|
| INCI Name | weight % |
| A | |
| Aqua | 22.00 |
| Acrylates copolymer | 2.50 |
| Triethanolamine | 0.20 |
| Disodium EDTA | 0.10 |
| Sodium Laureth-2 Sulfate | 27.50 |
| Cocamidopropyl Betaine | 6.00 |
| B | |
| Aqua | 18.00 |
| Sodium Laureth-2 Sulfate | 5.50 |
| Cocamidopropyl Betaine | 4.00 |
| Cocamide MEA | 1.20 |
| Ethylene Glycol Distearate | 3.00 |
| C | |
| Silicone Quaternium-20 | 1.00 |
| Soybean oil | 1.00 |
| Wheat Protein | 0.50 |
| *Cannabis Sativa* (Hemp) Seed Oil | 1.00 |
| DMDM Hydantoin | 0.50 |
| D | |
| Decyl Glucoside | 3.00 |
| Disodium Cocoamphodiacetate | 3.00 |
| Total | 100.00 |

Procedure:
1. Into a clean and sanitized stainless steel container equipped with propeller mixer, add water in Phase B
2. Add sodium laureth 2 sufate and betaine, heat up to 70 to 75 C, slowly add Cocamide MEA and EGDS, mix slowly while minimizing air incorporation. Mix until uniform, then cool down to room temperature.
3. In another clean and sanitized stainless steel tank equipped with propeller mixer, add water and the rest of ingredients of phase A one by one while minimizing air incorporation. Mix until uniform.
4. Add phase B slowly into Phase A. Mix until uniform
5. Premix Silicone Quaternium 20 and soybean oil until uniform, then add into Phase A+B, mix well. Add the rest of ingredients in Phase C one by one into Phase A+B until homogeneous while minimizing air incorporation.
6. Add ingredients in Phase D one by one. Adjust pH by using citric acid to pH=5.5~6.5, and adjust viscosity to 6,000 cps~12,000 cps by adding q.s. NaCl.

| Shampoo Formulation 2 in 1 Shampoo (Coacervate) FH183B | |
|---|---|
| INCI Name | weight % |
| A | |
| Aqua | 22.00 |
| Acrylates copolymer | 2.50 |
| Triethanolamine | 0.20 |
| Disodium EDTA | 0.10 |
| Sodium Laureth-2 Sulfate | 27.50 |
| Cocamidopropyl Betaine | 6.00 |
| B | |
| Aqua | 18.00 |
| Sodium Laureth-2 Sulfate | 5.50 |
| Cocamidopropyl Betaine | 4.00 |
| Cocamide MEA | 1.20 |
| Ethylene Glycol Distearate | 3.00 |
| C | |
| Silicone Quaternium-20 | 1.00 |
| Example 19 | 1.00 |
| Wheat Protein | 0.50 |
| *Cannabis Sativa* (Hemp) Seed Oil | 1.00 |
| DMDM Hydantoin | 0.50 |
| D | |
| Decyl Glucoside | 3.00 |
| Disodium Cocoamphodiacetate | 3.00 |
| Total | 100.00 |

Procedure:
1. Into a clean and sanitized stainless steel container equipped with propeller mixer, add water in Phase B
2. Add sodium laureth 2 sufate and betaine, heat up to 70 to 75 C, slowly add Cocamide MEA and EGDS, mix slowly while minimizing air incorporation. Mix until uniform, then cool down to room temperature.
3. In another clean and sanitized stainless steel tank equipped with propeller mixer, add water and the rest of ingredients of phase A one by one while minimizing air incorporation. Mix until uniform.
4. Add phase B slowly into Phase A. Mix until uniform
5. Premix Silicone Quaternium 20 and Example 19 until uniform, then add into Phase A+B, mix well. Add the rest of ingredients in Phase C one by one into Phase A+B until homogeneous while minimizing air incorporation.
6. Add ingredients in Phase D one by one. Adjust pH by using citric acid to pH=5.5~6.5, and adjust viscosity to 6,000 cps~12,000 cps by adding q.s. NaCl.

| Comparison | | |
|---|---|---|
| | FH183A | FH183B |
| Viscosity (cps) | 10,000 | 12,000 |
| pH | 5.72 | 5.70 |
| Appearance | Opaque white cream | Opaque white cream |

| Foam Evaluation | | | |
|---|---|---|---|
| Sample (average, mL) | Initial Reading | Two Minute Reading | Five Minute Reading |
| FH183A | 700 | 690 | 670 |
| FH183B | 700 | 690 | 680 |

The performance of the shampoos were quite different when compared to each other in terms of wet comb and after-feel when dry. The formulation containing the compound of the present invention were far superior than the one that did not.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claim be construed as encompassing all the features of patentable novelty which reside in the present invention, including all features which would be treated as equivalents thereof by those skilled in the art to which the invention pertains.

What is claimed:

1. A process for conditioning hair or skin which comprises contacting the hair or skin with an effective conditioning concentration of a polymer conforming to the following structure;

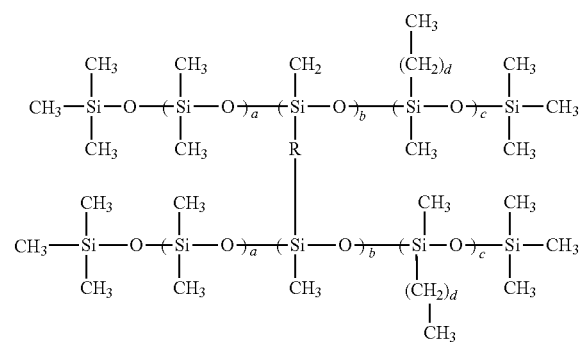

wherein:
a is an integer ranging from 1 to 200;
b is 1;
c is an integer ranging from 1 to 20;
d is an integer ranging from 11 to 15;
with the proviso that the ratio of a to c ranges from 1:1 to 10:1;
R is

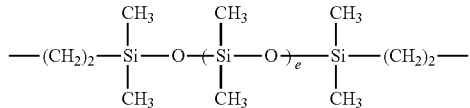

e is an integer ranging from 10 to 100.

2. A process of claim 1 wherein said effective conditioning concentration ranges from 0.1 to 20% by weight.
3. A process of claim 1 wherein d is 11.
4. A process of claim 1 wherein d is 15.
5. A process of claim 2 wherein d is 11.
6. A process of claim 2 wherein d is 15.

* * * * *